(12) United States Patent
Takase et al.

(10) Patent No.: US 8,068,651 B2
(45) Date of Patent: Nov. 29, 2011

(54) MEDICAL IMAGING DIAGNOSIS APPARATUS

(75) Inventors: Yasunori Takase, Yokohama (JP); Tatsuo Maeda, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 804 days.

(21) Appl. No.: 12/174,049

(22) Filed: Jul. 16, 2008

(65) Prior Publication Data

US 2009/0022265 A1 Jan. 22, 2009

(30) Foreign Application Priority Data

Jul. 18, 2007 (JP) ................................. 2007-187283

(51) Int. Cl.
*G06K 9/00* (2006.01)
(52) U.S. Cl. ........................................... 382/128; 378/8
(58) Field of Classification Search .......... 382/128–132; 378/4, 8, 16, 98, 98.2, 98.9, 98.11, 98.12, 378/901; 600/431
See application file for complete search history.

(56) References Cited

U.S. PATENT DOCUMENTS

| 5,459,769 A | 10/1995 | Brown ............................ 378/4 |
| 5,987,093 A | 11/1999 | Ozaki ........................... 119/705 |
| 6,188,744 B1 | 2/2001 | Shinohara et al. ................. 378/8 |
| 2003/0108149 A1 | 6/2003 | Tsuyuki ........................... 378/54 |
| 2004/0114706 A1 | 6/2004 | Ikeda et al. ........................ 378/4 |

FOREIGN PATENT DOCUMENTS

| EP | 1 712 181 A2 | 10/2006 |
| JP | 6-114049 | 4/1994 |
| JP | 11-342125 | 12/1999 |
| JP | 2004-113779 | 4/2004 |
| JP | 2005-245797 | 9/2005 |

*Primary Examiner* — Courtney Thomas
(74) *Attorney, Agent, or Firm* — Oblon, Spivak, McClelland, Maier & Neustadt, L.L.P.

(57) ABSTRACT

The medical imaging diagnosis apparatus includes: a region-of-interest setting unit configured to acquire an image of an examination target region in the body of a subject, and thus to set up, on the image, a region of interest, in which change in concentration of a contrast medium is observed; a calculator configured to calculate an average of CT values each representing the concentration of the contrast medium in the region of interest; an approximation unit configured to find an approximation for the region of interest on the basis of multiple CT values calculated by the calculator for the region of interest; and a comparison unit configured to compare a coefficient of the approximation with a value representing a setup condition beforehand stored, and to detect the timing of a definitive scan on the basis of the approximation which agrees with the setup condition within a predetermined range.

15 Claims, 6 Drawing Sheets

MEDICAL IMAGING DIAGNOSIS APPARATUS

CROSS REFERENCE TO RELATED APPLICATIONS

This application is based upon and claims the benefit of priority from prior Japanese Patent Application 2007-187283 filed on Jul. 18, 2007 the entire contents of which are incorporated by reference herein.

BACKGROUND OF THE INVENTION

1. Field of the Invention

The present invention relates to a medical imaging diagnosis apparatus which detects an optimal scan timing for radiographing and collecting information on the inside of the body of a subject by use of a contrast medium.

2. Description of the Related Art

In current practice, when information on the inside of the body of a subject is radiographed, for example, by use of an X-ray CT (computed tomography) apparatus, a contrast medium is administered to an examination (or tomography) target region. The tomography using a contrast medium makes the geography of the target region appear sharper in contrast than any other region administered with no contrast medium.

In such tomography using a contrast medium, the contrast medium is administered not directly to an examination (or tomography) target region, but to a region other than the examination target region through intravenous injection or the like. After administering the contrast medium, the examination target region is radiographed by timing the arrival of the administered contrast medium at the examination target region.

The easiest way to observe the change in concentration of the contrast medium in the examination (or tomography) target region is to determine the change in concentration of the contrast medium by paying attention to blood vessels through which the contrast medium flows. With this taken into consideration, generally, the change in concentration of the contrast medium is observed in the blood vessels through which the contrast medium flows to the examination target region from the region in which the contrast medium has been administered. This is because the observation and determination is designed to be carried out by use of a property of the contrast medium which makes a region administered with the contrast medium appear sharper in contrast than any other region administered with no contrast region, in other words, by use of change in brightness (corresponding to change in CT values) on the display screen of the X-ray CT apparatus. In order to carry out such an observation, for instance, an examiner sets up an observation target region (hereinafter referred to as a "region of interest (ROI)") in an appropriate blood vessel while checking on a fluoroscopic image generated, and radiographs the region (this type of radiography will be referred to as "scout scan" in contrast to "definitive scan" with which the examination target region is radiographed), thereby observing the change in concentration of the contrast medium in the region, as shown in Japanese Patent Application Publication Nos. Hei. 6-114049 (hereinafter referred as Document 1), Hei. 11-342125 (hereinafter referred to as Document 2) and 2004-113779 (hereinafter referred to as Document 3).

The time taken for the contrast medium to reach the examination target region after its administration varies depending on where the examination target region is. In addition, the time suitable for radiographing the examination target region is short. This makes it very difficult to evaluate whether or not the contrast medium has reached the examination target region. In some cases, for example, the target region may start to be radiographed before the contrast medium reaches the target region, or after the contrast medium has passed the target region.

For the purpose of preventing such a problem, Japanese Patent Application Publication No. 2005-245797 (hereinafter referred to as Document 4) discloses an X-ray CT apparatus including: a holder configured to hold an X-ray tube and an X-ray detector at their respective predetermined angles; a fluoroscopic image generator configured to generate a fluoroscopic image of the body of a subject taken in a predetermined direction on the basis of the dose of an X-ray beam which is continuously applied on the body of the subject from the X-ray tube thus held, and which is detected by the X-ray detector thus held; a display configured to display the fluoroscopic image thus generated; a determination unit configured to determine the start of a scan for tomography on the basis of change in concentration of a contrast medium in the fluoroscopic image.

Use of the X-ray CT apparatus of this type is considered to make it possible to obtain a tomographic image appropriately highlighting the geography of the predetermined region, and to reduce the radiation exposure dose on the body of the subject in comparison with the current practice using a pre-scan in the real prep scan method.

As to Documents 1, 2 and 4, however, it is considered to be difficult to observe the change in concentration of the contrast medium in the fluoroscopic image in determination of the start of a scan for tomography.

That is because only a single ROI is set up to observe the change in concentration of the contrast medium. This sometimes makes it difficult for even a skilled examiner to set up an ROI in an exact position on a blood vessel to be observed. If an ROI is not successfully set up on the blood vessel, for instance, when the ROI is unsuccessfully set up on a bone, it is impossible to observe the change in concentration. As a result, the examination target region is not appropriately radiographed. Depending on where the examination target region is, a blood vessel suitable for observing the change in the concentration is not always found. Moreover, in some cases, it is difficult to find an image representing blood vessels in the generated fluoroscopic image. In these cases, it is impossible even to set up an ROI.

According to Document 3, multiple ROIs are set up. The multiple ROIs are set up because a CT value of image data needs to be measured by means of a first low-dose X-ray scan (or a first scan), a high-dose X-ray scan (or a second scan) and a second low-dose X-ray scan (or a third scan) for the purpose of determining the timings of the start and end of a high-dose X-ray scan in the contract-enhanced dynamic CT. This makes it possible to grasp the start timing and the like with high exactness. On the other hand, this requires much labor and time. For this reason, it is impossible to easily set the start timing and the like.

The present invention has been made for the purpose of solving the above problems. An object of the present invention is to provide a medical imaging diagnosis apparatus capable of, when change in concentration of a contrast medium is observed prior to radiographing and collecting information on the inside of a body of a subject by using the contrast medium, more easily specifying a region including a blood vessel suitable for the observation of the change in concentration of the contrast medium, and thus of increasing the diagnosis efficiency, as well as of informing an operator of the optimal timing to scan an examination target region on the basis of the change in concentration in the region.

SUMMARY OF THE INVENTION

A medical imaging diagnosis apparatus according to an embodiment of the present invention is characterized by including: a region-of-interest setting unit configured to acquire an image of an examination target region in the body of a subject, and thus to set up, on the image, a region of interest, in which change in concentration of a contrast medium is observed; a calculator configured to calculate values each representing the concentration of the contrast medium in the region of interest; an approximation unit configured to find an approximation for the region of interest on the basis of multiple CT values calculated by the calculator; and a comparison unit configured to compare a coefficient of the approximation with a value representing a setup condition beforehand stored, and to detect the timing of a definitive scan on the basis of the approximation which agrees with the setup condition within a predetermined range.

DETAILED DESCRIPTION OF THE INVENTION

Detailed descriptions will be provided hereinbelow for an embodiment of the present invention by referring to the drawings.

Figure 1:
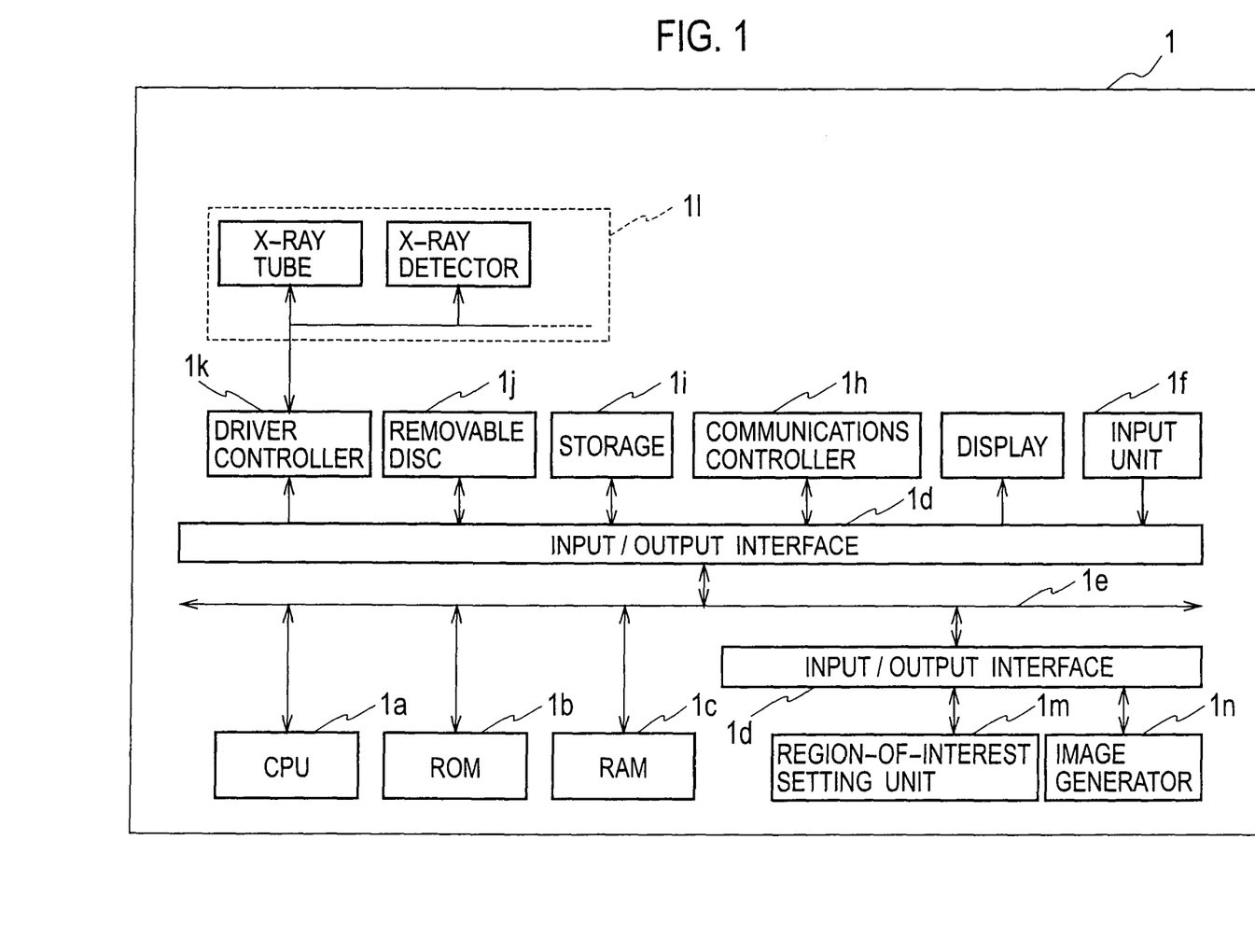
FIG. 1 is a block diagram showing an inner configuration of a medical imaging diagnosis apparatus according to an embodiment of the present invention.

FIG. 1 is a block diagram showing an inner configuration of a medical imaging diagnosis apparatus according to the embodiment of the present invention. The present invention is applicable to any type of medical imaging diagnosis apparatus as long as the apparatus is that which acquires a diagnostic image by use of a contrast medium. Descriptions will be provided for the embodiment of the present invention by taking an X-ray CT apparatus as an example to illustrate the medical imaging diagnosis apparatus 1.

In the medical imaging diagnosis apparatus 1, a CPU (Central Processing Unit) $1a$, a ROM (Read-Only Memory) $1b$, a RAM (Random-Access Memory) $1c$ and an input/output interface $1d$ are connected one to another through a bus $1e$. An input unit $1f$, a display $1g$, a communications controller $1h$, a storage $1i$, a removable disc $1j$ and a driver controller $1k$ are connected to the input/output interface $1d$. This driver controller $1k$ includes, for example, a driver $1l$ which includes an X-ray tube and an X-ray detector receiving an X-ray, which constitute the X-ray CT apparatus. The driver $1l$ is controlled by the driver controller $1k$. In addition, a region-of-interest setting unit $1m$ and an image generator $1n$ are connected to each other through the input/output interface $1d$, as well.

The CPU $1a$ is a processor for implementing a series of processes as follows. The CPU $1a$ reads a boot program for activating the medical imaging diagnosis apparatus 1 from the ROM $1b$ on the basis of an input signal from the input unit $1f$, and executes the boot program. Thus, the CPU $1a$ reads various operating systems stored in the storage $1i$. In addition, the CPU $1a$ controls various units through the input unit $1f$ and the input/output interface $1d$ on the basis of signals from other external apparatuses, which are not illustrated in FIG. 1. Furthermore, the CPU $1a$ reads programs and data stored in the RAM $1c$, the storage $1i$ and the like, as well as loads the RAM $1c$ with the programs and data. Moreover, the CPU $1a$ calculates and processes data on the basis of commands in programs read from the RAM $1c$.

The input unit if is configured of input devices, such as a keyboard and a dial, through which an operator (for example, a physician or an examiner) of the medical imaging diagnosis apparatus 1 inputs his/her various operations. The input unit $1f$ generates an input signal in accordance with an operation of the operator, and transmits the input signal to the CPU $1a$ through the bus $1e$. In addition to the keyboard and the like, a special operation panel is provided to the medical imaging diagnosis apparatus 1. The operator can input his/her operations onto an operation screen through an input device on the operation panel, as well.

An example of the display $1g$ is a liquid crystal display. This display $1g$ receives an output signal from the CPU $1a$ through the bus $1e$, and then displays: an image needed to set up ROIs for a scout scan, an image needed to set up various conditions for a definitive scan, or the like; or a result of a process carried out by the CPU $1a$, or the like.

Examples of the communications controller $1h$ are a LAN card, a modem and the like. The communications controller $1h$ enables the medical imaging diagnosis apparatus 1 to be connected to a communications network such as the Internet and a LAN (Local Area Network). As an input signal or an output signal, a set of data transmitted to, or received from, the communications network through the communications controller $1h$ is transmitted to, or received from, the CPU $1a$ through the input/output interface $1d$ and the bus $1e$.

The storage $1i$ is configured of a semiconductor memory or a magnetic disc. Programs and data which the CPU $1a$ executes are stored in the storage $1i$.

The removable disc $1j$ includes an optical disc and a flexible disc. A signal read or written by a disc drive is transmitted to, or received from, the CPU $1a$ through the input/output interface $1d$ and the bus $1e$.

The region-of-interest setting unit $1m$ sets up ROIs in which to observe change in the concentration of a contrast medium on the basis of an instruction of the operator. When the ROIs are set up, the region-of-interest setting unit $1m$ causes a setup screen to be displayed on the display $1g$. The operator sets up the ROIs in accordance with an ROI setup screen displayed on the display $1g$. For example, the operator sets up a region of interest in a region in the body of a subject depending on where an examination target region as a tomography target region is, and sets up the number of regions of interest which should be included within the outermost frame of the region of interest thus set up by the operator.

The image generator in generates an image of the body of a subject from electric signals generated by the X-ray detector configured to detect an X-ray which is applied on the body of the subject from the X-ray tube, and which is transmitted in the body of the subject body.

In the case of the medical imaging diagnosis apparatus 1, a timing detecting program is stored in the storage 1*i* or the removal disc 1*j*. The timing detecting program is read and executed by the CPU 1. Thereby, a timing detector 2 is implemented in the medical imaging diagnosis apparatus 1.

Figure 2:
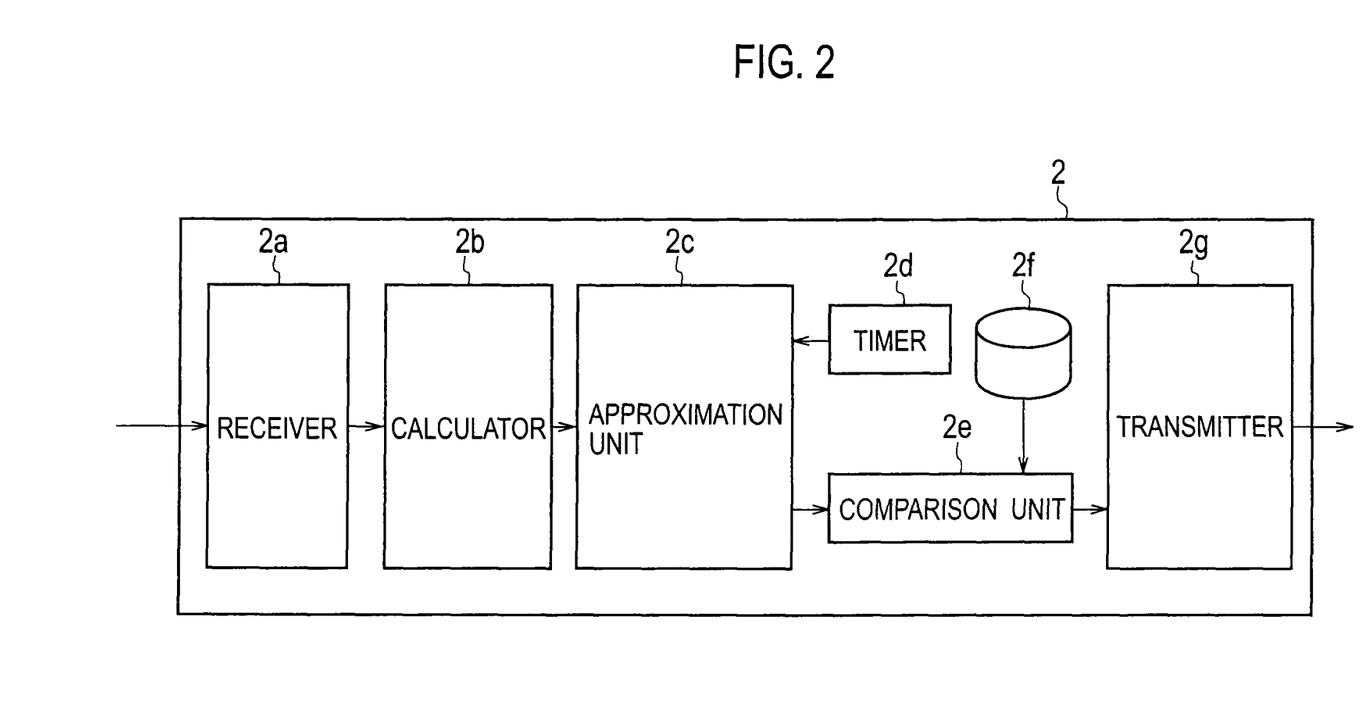
FIG. 2 is block diagram showing an inner configuration of a timing detector according to the embodiment of the present invention.

FIG. 2 is a block diagram showing a configuration of the timing detector 2 which is implemented in the medical imaging diagnosis apparatus 1. The timing detector 2 is configured of a receiver 2*a*, a calculator 2*b*, an approximation unit 2*c*, a timer 2*d*, a comparison unit 2*e*, a database 2*f* and a transmitter 2*g*. The timing detector 2 detects a timing of a definitive scan on the basis of change in CT values of the respective ROIs in the outermost frame which is set up by an operator by use of the region-of-interest setting unit 1*m*.

Figure 3:
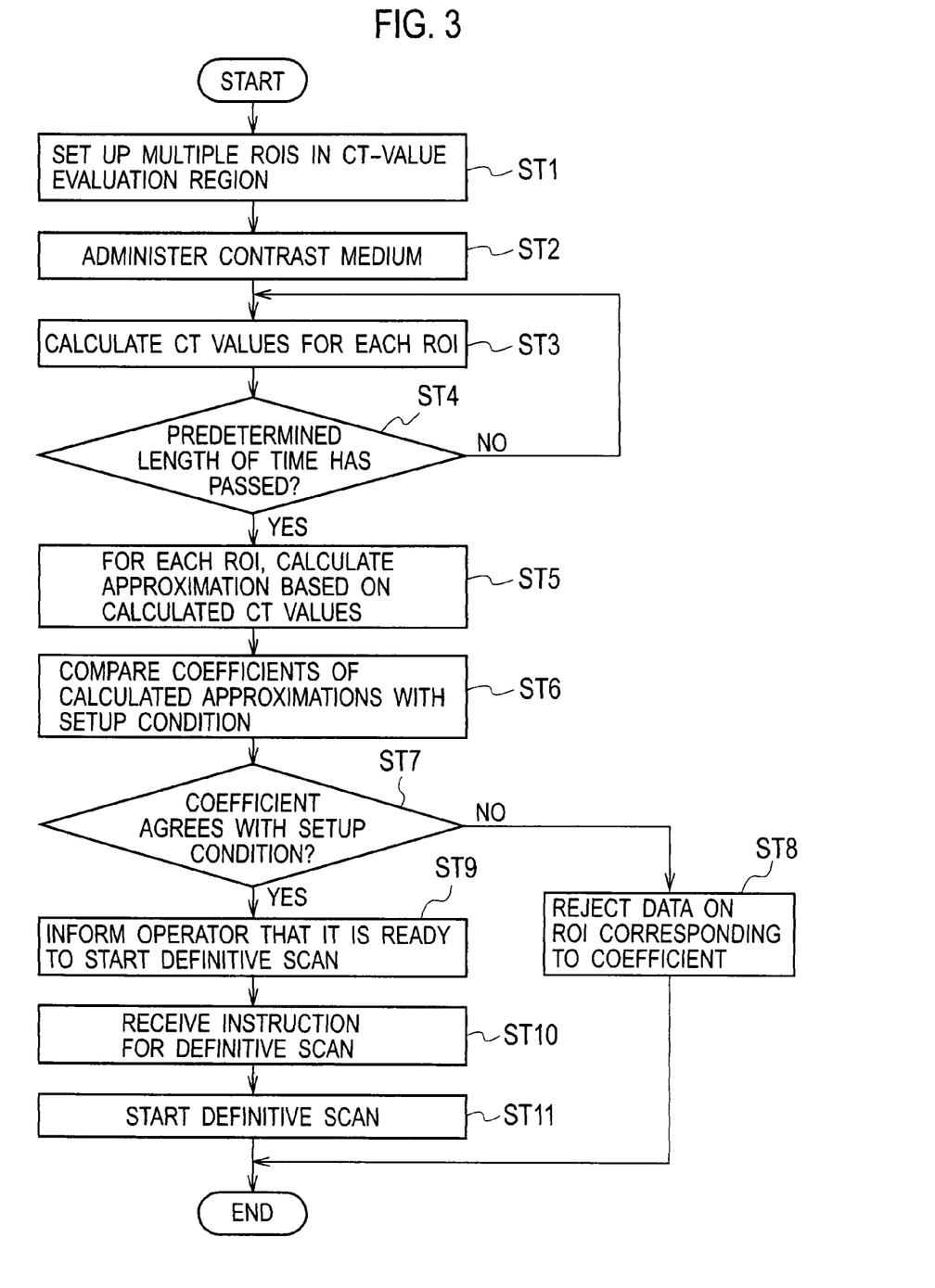
FIG. 3 is a flowchart showing a flow of the steps from a step of setting up an ROI through a step of starting a definitive scan.

Next, by use of a flowchart shown in FIG. 3 and the like, descriptions will be provided for a procedure in accordance with which the medical imaging diagnosis apparatus 1 detects a timing of a definitive scan, along with operations of components in the timing detector 2.

In a case where a region of the body of a subject as an examination target region is tomographed by use of a contrast medium, it is necessary to evaluate whether or not the contrast medium administered has reached the examination target region. The evaluation is necessary because a clear examination image can be obtained when the contrast medium makes the geology of the target examination region appear sharper than the neighboring organs, that is, when the target examination region appears sharper in contrast.

Suppose that a contrast medium administered to the body of a subject is observed in a region of the body thereof. The concentration value (corresponding to a CT value) of the contrast medium therein changes with time, for example, as shown by a graph in FIG. 4. Here, the CT value is a value of the X-ray attenuation coefficient of an organ or tissue inside the body of the subject (expressed in HU (Hounsfield Unit)) relative to the CT value of water, which is defined as zero. The organ or tissue is displayed more brightly (or whiter) as the CT value of the organ or tissue becomes larger. Generally speaking, tissues in the human body can be arranged in the following descending order of the CT value: ossification/calcification, coagulated blood, soft tissue, blood, water, fat, and air.

Figure 4:
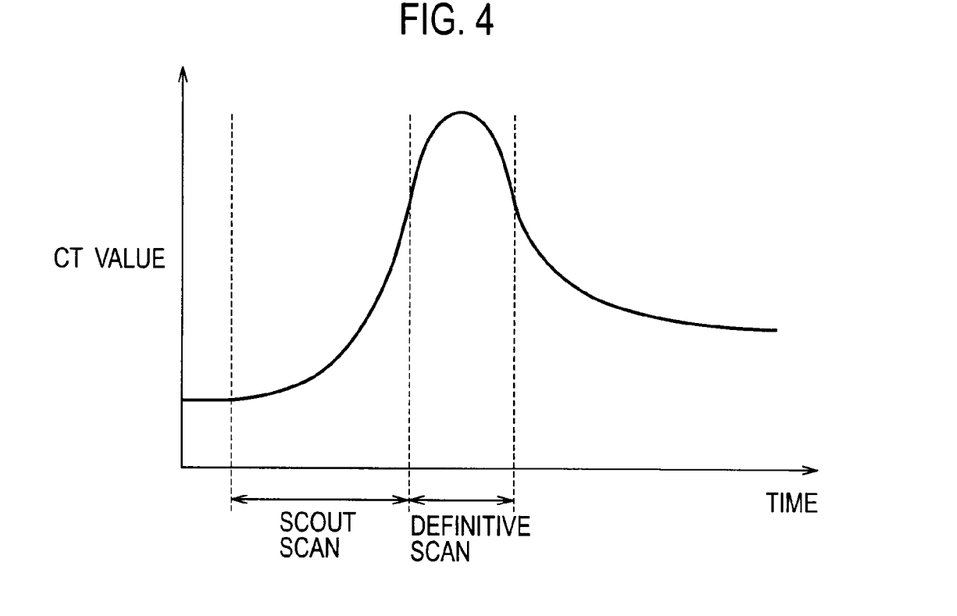
FIG. 4 is a graph showing an example of a CT value which changes with time.

Once a contrast medium is administered, the CT value gradually increases. Then, after a certain length of time has passed, the CT value gradually decreases. The definitive scan is made while the CT value is high as shown in FIG. 4, or while the contrast makes the examination target region appear sharper in contrast than the neighboring organs after its arrival in the examination target region. With this taken into consideration, an optimal timing of a definitive scan is detected by performing a scout scan before the definitive scan.

Figure 5:
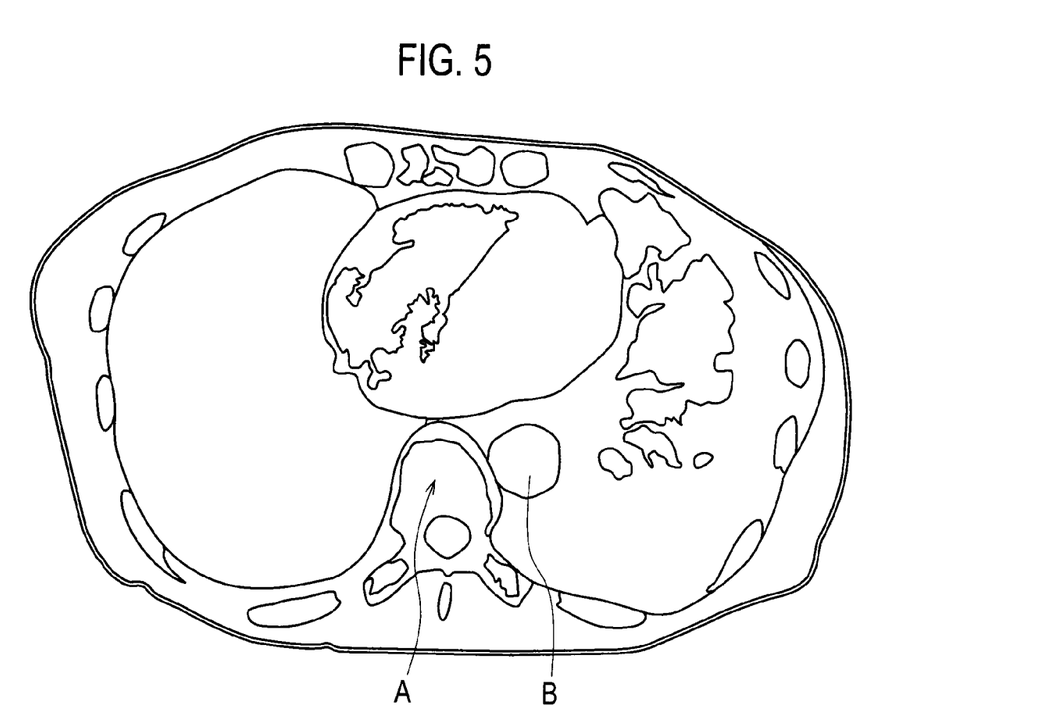
FIG. 5 is a schematic diagram of an image produced by a medical imaging diagnosis apparatus.

First of all, the image generator in prepares an image by reconstructing information on the body of the subject which is radiographed. The operator sets up a region in which to measure the CT value, or a region of interest (ROI), on this image by use of the region-of-interest setting unit 1*m* (in step ST1). FIG. 5 is a schematic diagram of an image radiographed by use of an X-ray CT apparatus. This schematic diagram shows an image obtained by reconstructing information on the abdomen of a subject which is radiographed in a direction perpendicular to the body axis of the subject. A part located near the center portion of the schematic diagram, and which looks rising toward the center portion thereof from the right and left sides, is a spine A. What looks like a circle in the right of the spine A is an aorta abdominalis B.

Because, as described above, the contrast medium reaches the examination target region through blood vessels after administered to the body of the subject, it is appropriate to set up the ROI in a part of one of the blood vessels for the purpose of observing the change in concentration of the contrast medium, or the change in CT value. The schematic diagram of FIG. 5 shows the aorta abdominalis B in a certain large size. In some cases, depending on where an examination target region is located, a blood vessel in which to observe change in CT value may be too small, or a blood vessel may not be able to be displayed by use of the display 1*g* because the blood vessel is located behind some organ.

With this taken into consideration, in the case of present embodiment, the operator sets up only the largest possible frame (or the outermost frame) before setting up regions of interest. The region of interest setting unit 1*m* includes an entry section which requests the operator to specify how many ROIs the inside of the outermost frame should be divided. After the outermost frame is set up, the region-of-interest setting unit 1*m* automatically sets up multiple ROIs in the outermost frame by dividing the inside of the outermost frame into ROIs in accordance with a number, for example, 8, 16, 24 or the like, which the operator specifies.

Figure 6:
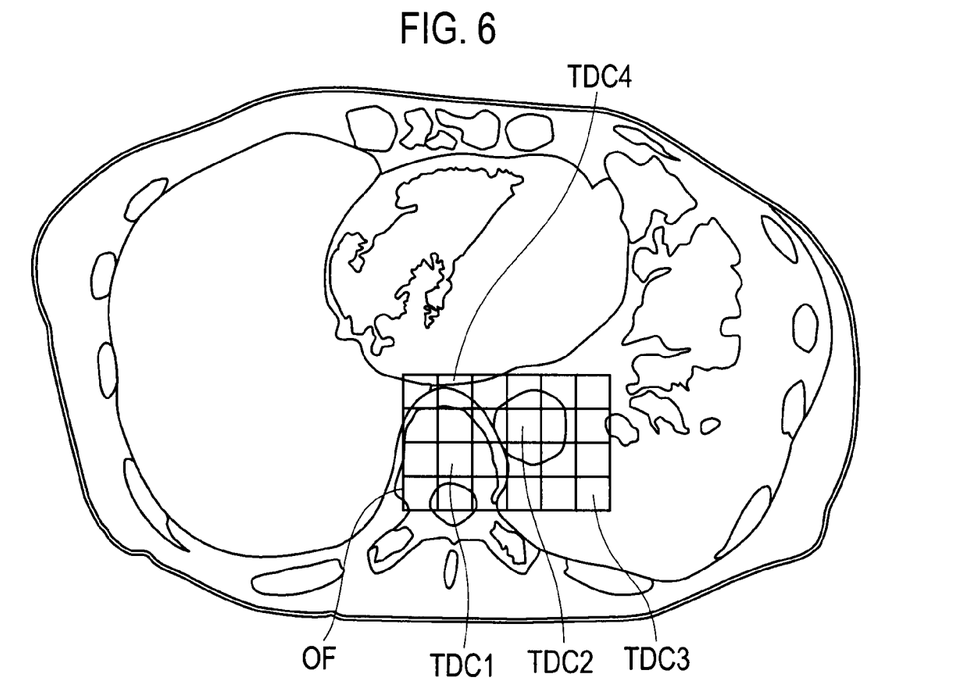
FIG. 6 is a schematic diagram showing how rectangular ROIs are set up in the schematic diagram shown in FIG. 5.

FIG. 6 is a schematic diagram showing how an outermost frame OF is set up in such a way that the aorta abdominalis is covered by regions of interest, and concurrently how multiple ROTs are set up by dividing the inside of the outermost frame into 24 small rectangles. In this respect, 24 is a product of 4 in the vertical direction and 6 in the horizontal direction. As described above, only an outermost frame is set up first, and multiple small ROIs are automatically set up in the outermost frame. This scheme makes it possible to solve difficulty with which the operator finds an appropriate blood vessel and sets up appropriate ROIs on the blood vessel. At this time, it is desirable that the size of each of the multiple small ROIs should be set smaller than the diameter of a blood vessel in which to measure the change in the concentration value of the contrast medium.

Furthermore, an area covered by each ROI needs to be set smaller than the size of the blood vessel on which to set up the ROI for the purpose of calculating the change in CT value of the contrast medium more exactly. The method of setting up ROIs according to the present embodiment makes it possible to position an ROI inside the blood vessel with ease.

Figure 7:
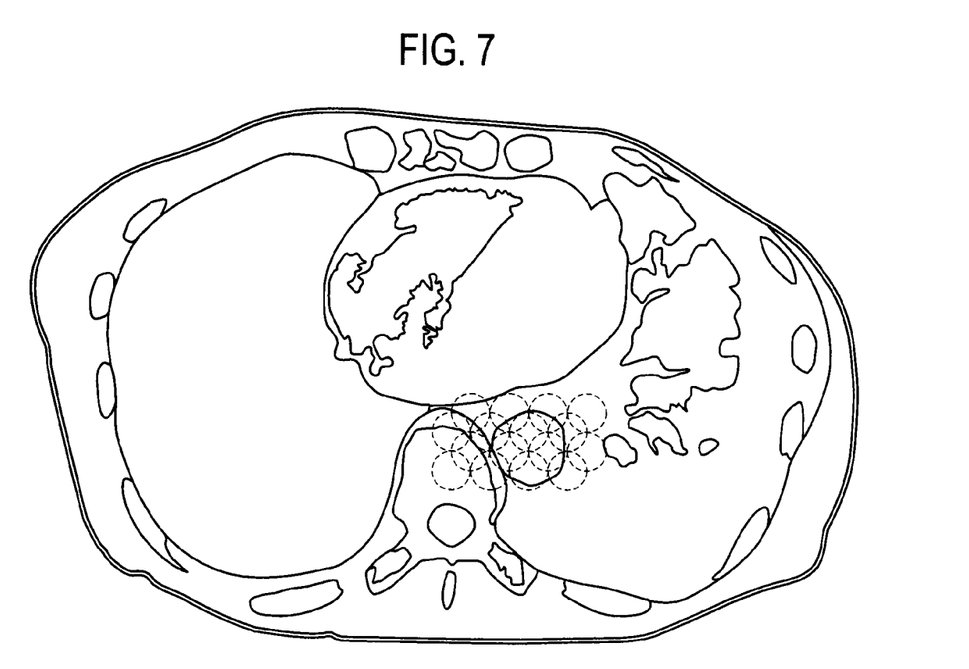
FIG. 7 is a schematic diagram showing how circular ROIs are set up in the schematic diagram shown in FIG. 5.

FIG. 6 shows how rectangular ROIs are set up by dividing the inside of the outermost frame OF into the rectangular ROIs. However, each blood vessel is shaped like a circle. With this shape taken into consideration, as shown in FIG. 7, circular ROIs are set up in the inside of the outermost frame OF in such a way that the circular ROIs overlap each other. The forming of the ROIs in such a shape makes it possible to measure all of the CT values in the blood vessel. It should be noted that the ROIs may be formed not only in the shape of a rectangle or a circle but also in any other arbitrary shape.

Once the ROIs are set up, a contrast medium is administered to the subject (in step ST2). Once the contrast medium is administered, the calculator 2*b* in the timing detector 2 calculates CT values of the respective ROIs discretely (in step ST3). Each CT value is calculated by measuring the brightness of each of the pixels included in each corresponding one of the ROIs displayed on the display 1*g*. The brightness increases as the concentration of the contrast medium increases.

In the case of the present embodiment, the CT value of each ROI is obtained as follows. The brightness is found for each of the pixels included in the ROI. Subsequently, the brightness of each pixel is added up for the ROI. Thereafter, the aggregate brightness of the ROI is divided by the number of pixels included in the region covered by the ROIs. As a result, the thus obtained average CT value is used as the CT value of the ROI. Instead of this method, another method can be adopted to calculate the CT value of each ROI. The CT value of each ROI can be obtained using an alternative method as follows. First of all, an average of CT values of the respective pixels included in each ROI is calculated. Subsequently, the average of CT values not smaller than the average CT value is calculated. As result, the thus calculated average is used as the CT value of the ROI. The CT value of each ROI can be obtained using another alternative method as follows. First of all, a histogram is calculated for the ROI. Subsequently, out of all of the CT values of the respective pixels included in the ROI, larger CT values are selected out in such away that, for example, the number of selected CT values constitutes 50% of the entire CT values. Thereafter, the average of the selected CT values is calculated. As a result, the thus calculated average is used as the CT value of the ROI.

For each ROI, the CT value calculated by the calculator $2b$ is stored, for example, in the approximation unit $2c$, and is used as a set of data when an approximation is found. The CT values thus calculated for the respective ROIs may be stored in any type of format, such as in a table.

Figure 8:
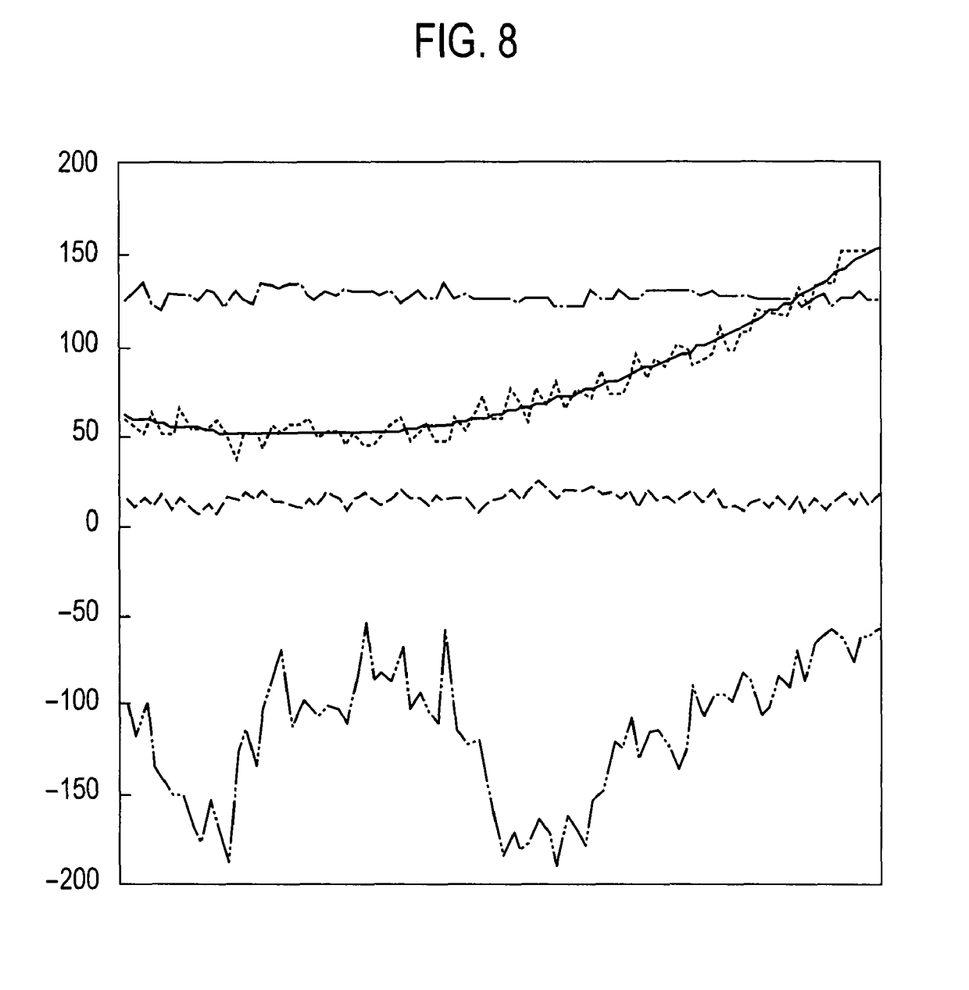
FIG. 8 is a TDC (time-density-curve) schematic diagram graphing CT values calculated for the respective ROIs.

The CT values thus calculated may be graphed, for example, as shown in FIG. 8. Curves, shown in FIG. 8, which reflect changes in the respective CT values are termed as TDCs (Time-Density Curves). A TDC is shown for each ROI. In this graph, the axis of ordinates indicates the scale of the CT value from −200 to 200, where the CT value of water is defined as zero. On the other hand, the axis of abscissas indicates time. It should be noted that the graph of FIG. 8 is introduced for the purpose of showing what a TDC is. In the embodiment of the present invention, no graph is designed to be displayed on the display $1g$. However, this type of graph may be designed to be displayed on the display $1g$.

Although the TDCs are produced for the set-up ROIs, respectively, the graph of FIG. 8 shows only four TDCs which are selected out of the set-up ROIs. These four TDCs are referred to as a first to fourth TDCs from the top to the bottom of the graph for the explanatory convenience. Out of the four TDCs, only the fourth TDC jumps up and down in the minus area, whereas the first and third TDCs are shown as being almost straight. The second TDC is shown as a curve rising roughly from left to right. Incidentally, FIG. 6 shows where the ROIs for which the first to fourth TDCs are set up are located. In FIG. 6, the first TDC corresponds to the CT value of the spine A, and the second TDC corresponds to the CT value of the aorta abdominalis B.

Thereafter, on the basis of time information transmitted from the timer $2d$, the approximation unit $2c$ checks on whether or not a predetermined length of time has passed (in step ST4). That is because, if the number of CT values sampled for the base of each approximation calculated by the approximation unit $2c$ is small, a precise determination can not be made. The approximation unit $2c$ continues collecting CT values for each ROIs calculated by the calculator $2b$, until the predetermined length of time passes (in the case of NO in step ST4). Incidentally, the predetermined length of time can be set up arbitrarily.

Once the predetermined length of time passes (in the case of YES in step ST4), the approximation unit $2c$ finds an approximation for each TDC on the basis of the CT values found for each corresponding ROI by use of the method of least squares (in step ST5). For the second TDC, for example, the following approximation can be found on the basis of CT values found for the second TDC.

$$y=0.0272x^2-1.1469x+61.606$$

Before the approximations are found, various conditions can be set up for the purpose of detecting a definitive scan timing more exactly. In the embodiment of the present invention, the approximation for each ROI is found by use of 30 CT values collected before the approximation is started. In addition, a condition that the square of the residual is equal to or more than 0.85 is used for the purpose of using the method of least squares.

Once the approximation unit $2c$ finds the approximations for the respective TDCs, the approximation unit $2c$ transmits the approximations to the comparison unit $2e$. Through comparison, the comparison unit $2c$ checks on whether or not the coefficient of each of the approximations transmitted from the approximation unit $2c$ satisfies a reference value (hereinafter referred to as a "setup condition") which has been beforehand set up, and which is recorded in the database $2f$ (in step ST6).

In the embodiment of the present invention, the following conditions are adopted together. First, the difference between the earliest calculated CT value and the latest calculated CT value is equal to or more than 20 HUs. Second, an average of the 5 consecutive CT values right after the approximation is started is equal to or less than 120 HUs. Third, all of the CT values other than the foregoing 30 CT values are equal to or less than 120 HUs for the purpose of removing the artifact. In addition, sets of data are selected with the following conditions, and are used as comparison objects. A first condition is that, for the purpose of reducing influence of CT values of each of ROIs which happen to be set up on vessels, CT values less than 0 HU and CT values more than 250 HUs are both excluded. A second condition is that, for the purpose of avoiding influence of increase in CT value of each of ROIs which happen to be set up on bones (signal of CT values of an ROI on a bone is similar to, but not the same as, that of an ROI on a vessel), if a ROI includes 10 or more pixels whose CT values are more than 250 HUs, no such CT values are used for the ROI.

It is likely that these conditions may be different from one region to another, in which the ROIs are set up by the region-of-interest setting unit $1m$. For this reason, the conditions are designed to be set up arbitrarily for each set-up ROI. The comparison unit $2e$ makes the foregoing comparison for each multiple ROIs set up by the region-of-interest setting unit $1m$.

When the comparison unit $2e$ compares the setup condition stored in the database $2f$ with the coefficient of the approximation calculated for an ROI, in the case where the coefficient does not meet the setup condition (in the case of NO in step ST7), the comparison unit $2e$ does not adopt the approximation of the ROI as a reference when the definitive scan timing is detected (in step ST8). On the other hand, in the case where the coefficient meets the setup condition (in the case of YES in step ST7), the comparison unit $2e$ informs the operator that the examination target region is ready for being radiographed (as a definitive scan) (in step ST9). The display $1g$ may be used as an informing unit like in the case of the embodiment of the present invention. Otherwise, an informing unit may be separately provided to the medical imaging diagnosis apparatus 1. The operator may be informed of the readiness not only through a screen by use of the display $1g$, but also with sounds together with the screen.

FIG. 8 shows the four TDCs including the first to fourth TDCs. In FIG. 8, a curve shown to overlap the second TDC is a curve satisfying the setup condition which is stored in the database $2f$. The comparison unit $2e$ detects the definitive scan timing by comparing the coefficient of this curve with the coefficients of the approximations respectively found for the TDCs. Incidentally, the comparison unit 2e does not determine that a region in which the ROI indicated by the TDC corresponding to this curve is set up is the blood vessel (the aorta abdominalis B in the case of the embodiment of the present invention). However, by reviewing the approximation of the ROI set up on the blood vessel, it is possible to detect an optimal timing of a definitive scan. For this reason, it is possible to determine that the region in which the ROI indicated by the TDC meeting the setup condition is the blood vessel as a result of the review.

Once the operator is informed of the readiness, the operator sets up radiographing conditions necessary for the definitive scan, and subsequently gives the medical imaging diagnosis apparatus 1 instruction to start the definitive scan. Upon reception of the instruction (in step ST10), the medical imaging diagnosis apparatus 1 starts the definitive scan in accordance with the set-up radiographing conditions (in step ST11).

In the embodiment of the present invention, as described above, permission to advance from the scout scan to the definitive scan (through steps ST9 to step ST11) is requested from the operator. However, the medical imaging diagnosis apparatus 1 may be configured to automatically advance to the definitive scan (or to automatically jump from step ST7 to step ST 11 directly) without requesting the permission from the operator if the coefficient of the approximation meets the setup condition. In other words, in a case where, as a result of the comparison made by the comparison unit 2e, the coefficient of the approximation meets the setup condition, the comparison unit 2e automatically generates a signal for starting the definitive scan, and transmits the signal to the medical imaging diagnosis apparatus 1. On the basis of this signal, the medical imaging diagnosis apparatus 1 starts the definitive scan in accordance with conditions set up in advance.

As described above, the embodiment of the present invention can provide a medical imaging diagnosis apparatus capable of: when change in concentration of a contrast medium is observed prior to radiographing and collecting information on the inside of a body of a subject by using the contrast medium, easily specifying an ROI covering a blood vessel suitable for the observation of the change in concentration of a contrast medium by simply setting up an outermost frame; thus increasing the diagnosis efficiency; and informing an operator of an optimal timing to scan an examination target region on the basis of the change in the concentration in the ROI.

The present invention is not limited to the foregoing embodiment as it is. When the present invention is carries out, the present invention can be embodied by modifying any one or all of the component elements thereof within the range not departing from the gist of the present invention. In addition, various inventions can be embodied by combining some of the component elements disclosed as being included in the foregoing embodiment whenever deemed necessary. For example, some of the component elements may be excluded from the component elements disclosed as being included in the embodiment. Furthermore, for the purpose of carrying out the invention as another embodiment, component elements may be combined with the component elements disclosed as being included in the present embodiment whenever deemed necessary.

What is claimed is:

1. A medical imaging diagnosis apparatus comprising:
    a region-of-interest setting unit configured to acquire an image of an examination target region in the body of a subject, and to set up, on the image, a region of interest, in which change in concentration of a contrast medium is observed;
    a calculator configured to calculate concentration values each representing the concentration of the contrast medium in the region of interest;
    an approximation unit configured to find an approximation for the region of interest on the basis of the plurality of concentration values calculated by the calculator; and
    a comparison unit configured to compare a coefficient of the approximation with a value representing a setup condition beforehand stored, and to detect timing of a definitive scan on the basis of the approximation which agrees with the setup condition within a predetermined range.

2. The medical imaging diagnosis apparatus according to claim 1, further comprising an informing unit configured to inform an operator of the timing of the definitive scan, the timing detected by the comparison unit.

3. The medical imaging diagnosis apparatus according to claim 1, wherein the comparison unit generates a signal to automatically start the definitive scan on the basis of the timing.

4. The medical imaging diagnosis apparatus according to claim 1, wherein, by setting up an outermost frame, the region-of-interest setting unit automatically divides the inside of the outermost frame into a plurality of regions beforehand specified, and thus sets up a plurality of small regions of interest.

5. The medical imaging diagnosis apparatus according to claim 2, wherein, by setting up an outermost frame, the region-of-interest setting unit automatically divides the inside of the outermost frame into a plurality of regions beforehand specified, and thus sets up a plurality of small regions of interest.

6. The medical imaging diagnosis apparatus according to claim 3, wherein, by setting up an outermost frame, the region-of-interest setting unit automatically divides the inside of the outermost frame into a plurality of regions beforehand specified, and thus sets up a plurality of small regions of interest.

7. The medical imaging diagnosis apparatus according to claim 1, further comprising:
    an X-ray tube,
    an X-ray detector configured to receive an X-ray which is applied from the X-ray tube to, and then transmitted through, the body of the subject; and
    an image generator configured to generate an image of the body of the subject from an electric signal generated by the X-ray detector.

8. The medical imaging diagnosis apparatus according to claim 2, further comprising:
    an X-ray tube,
    an X-ray detector configured to receive an X-ray which is applied from the X-ray tube to, and then transmitted through, the body of the subject; and
    an image generator configured to generate an image of the body of the subject from an electric signal generated by the X-ray detector.

9. The medical imaging diagnosis apparatus according to claim 3, further comprising:
    an X-ray tube,
    an X-ray detector configured to receive an X-ray which is applied from the X-ray tube to, and then transmitted through, the body of the subject; and an image generator configured to generate an image of the body of the subject from an electric signal generated by the X-ray detector.

10. The medical imaging diagnosis apparatus according to claim 4, further comprising:
   an X-ray tube,
   an X-ray detector configured to receive an X-ray which is applied from the X-ray tube to, and then transmitted through, the body of the subject; and
   an image generator configured to generate an image of the body of the subject from an electric signal generated by the X-ray detector.

11. The medical imaging diagnosis apparatus according to claim 5, further comprising:
   an X-ray tube,
   an X-ray detector configured to receive an X-ray which is applied from the X-ray tube to, and then transmitted through, the body of the subject; and
   an image generator configured to generate an image of the body of the subject from an electric signal generated by the X-ray detector.

12. The medical imaging diagnosis apparatus according to claim 6, further comprising:
   an X-ray tube,
   an X-ray detector configured to receive an X-ray which is applied from the X-ray tube to, and then transmitted through, the body of the subject; and
   an image generator configured to generate an image of the body of the subject from an electric signal generated by the X-ray detector.

13. A medical imaging diagnosis apparatus which sets up a start or stop timing of a definitive scan on the basis of change in concentration of a contrast medium, comprising:
   a region-of-interest setting unit configured to acquire an image of an examination target region of the body of a subject, and to set up, on the image, a plurality of regions of interest, in each of which change in concentration of a contrast medium is observed;
   a calculator configured to calculate concentration values each representing the concentration of the contrast medium in each of the regions of interest;
   an approximation unit configured to find coefficients of approximations for the regions of interest on the basis of the time changes in concentration values calculated by the calculator, respectively; and
   a comparison unit configured to find a region of interest which corresponds to an artery on the basis of the coefficients, and thus to detect a timing of a definitive scan on the basis of values each representing the concentration in the region of interest.

14. A medical imaging diagnosis apparatus which controls a scan timing on the basis of information on concentration of a contrast medium in medical images, comprising:
   an image generator configured to generate time-series medical images;
   a region setting unit configured to set up a plurality of small regions in each of the medical images;
   a calculator configured to find information on concentration of a contrast medium in the plurality of small regions;
   a selector configured to select small regions, which are going to be used to determine a timing of a definitive scan, out of the plurality of small regions on the basis of the information on the concentration; and
   a unit configured to determine the timing of the definitive scan on the basis of the information on the concentration of the contrast medium in the small regions selected by the selector.

15. A medical imaging diagnosis apparatus which controls display of a graph showing change in concentration of a contrast medium on the basis of information on the concentration of the contrast medium in medical images, comprising:
   an image generator configured to generate time-series medical images;
   a region setting unit configured to set up a plurality of small regions in each of the medical images;
   a calculator configured to find information on concentration of a contrast medium in the plurality of small regions;
   a selector configured to select small regions, which are going to be used to generate a graph showing change in the concentration, out of the plurality of small regions on the basis of the information on the concentration;
   a unit configured to find the graph showing the change in the concentration on the basis of the information on the concentration of the contrast medium in the small regions selected by the selector; and
   a display configured to display the graph showing the change in the concentration.

\* \* \* \* \*